United States Patent
Morisaki et al.

(10) Patent No.: US 11,058,608 B2
(45) Date of Patent: *Jul. 13, 2021

(54) CURABLE COMPOSITION FOR DENTAL USE, AND METHOD FOR PRODUCING SAME

(71) Applicant: TOKUYAMA DENTAL CORPORATION, Tokyo (JP)

(72) Inventors: Hiroshi Morisaki, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/605,617

(22) PCT Filed: Apr. 16, 2018

(86) PCT No.: PCT/JP2018/015734
§ 371 (c)(1),
(2) Date: Oct. 16, 2019

(87) PCT Pub. No.: WO2018/194031
PCT Pub. Date: Oct. 25, 2018

(65) Prior Publication Data
US 2020/0129384 A1    Apr. 30, 2020

(30) Foreign Application Priority Data
Apr. 18, 2017  (JP) .............................. JP2017-082024

(51) Int. Cl.
*A61K 6/887*  (2020.01)
*A61K 6/76*   (2020.01)
*A61K 6/17*   (2020.01)
*C08F 122/20* (2006.01)
*C08F 122/22* (2006.01)
*C08K 3/34*   (2006.01)
*C08K 7/18*   (2006.01)

(52) U.S. Cl.
CPC .............. *A61K 6/887* (2020.01); *A61K 6/17* (2020.01); *A61K 6/76* (2020.01); *C08F 122/20* (2013.01); *C08F 122/22* (2013.01); *C08K 3/34* (2013.01); *C08K 7/18* (2013.01); *C08K 2003/343* (2013.01); *C08K 2201/005* (2013.01)

(58) Field of Classification Search
CPC ........................................................ A61K 6/17
See application file for complete search history.

(56) References Cited

U.S. PATENT DOCUMENTS

| | | |
|---|---|---|
| 3,729,313 A | 4/1973 | Smith |
| 3,741,769 A | 6/1973 | Smith |
| 4,020,557 A | 5/1977 | Rockett et al. |
| 5,545,676 A | 8/1996 | Palazzotto et al. |
| 2004/0180983 A1 | 9/2004 | Hara et al. |
| 2008/0319104 A1 | 12/2008 | Klapdohr et al. |
| 2011/0196062 A1 | 8/2011 | Craig |
| 2013/0096226 A1* | 4/2013 | Toriyabe ................ A61K 6/887 523/115 |
| 2013/0172441 A1 | 7/2013 | Takahata et al. |
| 2014/0206792 A1 | 7/2014 | Ishizaka et al. |
| 2014/0213687 A1 | 7/2014 | Yamazaki et al. |
| 2014/0295376 A1 | 10/2014 | Uchida et al. |
| 2015/0094396 A1 | 4/2015 | Nakatsuka et al. |
| 2015/0272833 A1 | 10/2015 | Toriyabe et al. |
| 2017/0049665 A1 | 2/2017 | Kita et al. |
| 2017/0196667 A1 | 7/2017 | Teramae et al. |
| 2018/0303721 A1 | 10/2018 | Akizumi et al. |
| 2019/0192386 A1 | 6/2019 | Fukudome et al. |

FOREIGN PATENT DOCUMENTS

| | | |
|---|---|---|
| EP | 1236459 A1 | 9/2002 |
| EP | 2583660 A1 | 4/2013 |
| EP | 2902007 A1 | 8/2015 |
| EP | 3366269 A1 | 8/2018 |
| EP | 3536302 A1 | 9/2019 |
| JP | S62-086003 A | 4/1987 |

(Continued)

OTHER PUBLICATIONS

H. Matsumura et al., "Adhesion Yearbook 2006," 1st Edition, Quintessence Publishing Co., Ltd., Aug. 2006, pp. 129-137 (14 pages) with partial translation.
M. Miyazaki, "Science & Technique of Composite Resin Restoration," 1st Edition, Quintessence Publishing Co., Ltd., Jan. 2010, pp. 48-49 (6 pages) with partial translation.
Japanese Dental Technologists Association, 2011, No. 503, pp. 5-8, non-official translation (Yamakawa, Junichiro, New Standard of Hybrid Arising form Pursuit of Lasting Aesthetics—Hybrid-type Hardness Region (pearl aesthetics)) (6 pages).
International Search Report issued in corresponding International Application No. PCT/JP2018/015734; dated Jun. 12, 2018 (2 pages).
Written Opinion of the International Searching Authority issued in corresponding International Application No. PCT/JP2018/015734; dated Jun. 12, 2018 (3 pages).

(Continued)

*Primary Examiner* — Michael F Pepitone
(74) *Attorney, Agent, or Firm* — Osha Bergman Watanabe & Burton LLP

(57) ABSTRACT

Provided is a method for producing a dental curable composition, the method includes mixing a polymerizable monomer (A); a spherical filler (B) having an average primary particle diameter within a range of 230 nm to 290 nm; a spherical filler (C) having an average primary particle diameter within a range of 100 nm to 500 nm, the spherical filler having an average primary particle diameter different from that of the spherical filler (B); and a polymerization initiator (D), in which 90% or more in number of the individual particles constituting the spherical filler (B) and the spherical filler (C) are present in a range of ±5% from the average primary particle diameter, and the refractive indices of the spherical filler (B) and the spherical filler (C) are larger than the refractive index of a polymer of a polymerizable monomer (A).

16 Claims, No Drawings

(56) References Cited

FOREIGN PATENT DOCUMENTS

| JP | S63-218703 A | 9/1988 |
|---|---|---|
| JP | S63-273602 A | 11/1988 |
| JP | 2001239661 A | 9/2001 |
| JP | 2004276492 A | 10/2004 |
| JP | 2005-089729 A | 4/2005 |
| JP | 2006117543 A | 5/2006 |
| JP | 2007-532518 A | 11/2007 |
| JP | 2012-505823 A | 3/2012 |
| JP | 2012-087086 A | 5/2012 |
| JP | 2012-153640 A | 8/2012 |
| JP | 2014189503 A | 10/2014 |
| JP | 2015067594 A | 4/2015 |
| JP | 2016-169180 A | 9/2016 |
| RU | 2472708 C2 | 1/2013 |
| WO | 2009014031 A1 | 1/2009 |
| WO | 2011158742 A1 | 12/2011 |
| WO | 2012042911 A1 | 4/2012 |
| WO | 2012176877 A1 | 12/2012 |
| WO | 2013/039169 A1 | 3/2013 |
| WO | 2014/050634 A1 | 4/2014 |
| WO | 2015125470 A1 | 8/2015 |
| WO | 2017069274 A1 | 4/2017 |
| WO | 2018043595 A1 | 3/2018 |
| WO | 2018/101236 A1 | 6/2018 |

OTHER PUBLICATIONS

Office Action issued in corresponding Brazilian Application No. BR1120190094563, dated Jul. 1, 2020 (47 pages).
Extended European Search Report issued in the European Application No. 17876044.3, dated Oct. 25, 2019 (13 pages).
H. Shinoda et al., "Shikisai Kogaku Nyumon", Morikita Publishing Co., Ltd., 1st print published on May 1, 2007, pp. 73-78 with Partial English Translation (10 pages).
K. Saito, "Hikari to Shikisai no Kagaku", Kodansha, Ltd., 1st print published on Oct. 20, 2010, pp. 118-139, with Partial English Translation (21 pages).
The Color Science Association of Japan, ed., "Handbook of Color Science (3rd Edition)", University of Tokyo Press, published in Apr. 2011, pp. 1130-1181, with Partial English Translation (35 pages).
"Names of non-luminous object colours", JIS Z8102, revised Mar. 20, 2001, pp. 1-25 with Partial English Translation (16 pages).
"Colour specification—Names of light-source colours", JIS Z8110, revised Mar. 1, 1995, pp. 1-13, with Partial English Translation (9 pages).
H. Hosoda, "Basics of Photopolymerizable Composite Resins and Clinics", Nippon Shika Shuppan Co., Feb. 10, 1986, pp. 9-20, with Partial English Translation (9 pages).
T. Yamaoka, "Dictionary of Applied Optical Technologies and Materials", published by Industrial Technical Service Center Co., Ltd., Apr. 26, 2006, pp. 108-112, with Partial English Translation (4 pages).
Chemical Society of Japan, ed., "Chemistry Handbook, Fundamentals—II, Third Revision", published by Maruzen, Inc., Jun. 25, 1984, pp. 337-345 (5 pages).
International Search Report including Written Opinion issued in the International Application No. PCT/JP2018/008396, dated Apr. 17, 2018 (20 pages).
Office Action issued in the U.S. Appl. No. 16/605,602, dated Jun. 5, 2020 (10 pages).
International Search Report including Written Opinion issued in the International Application No. PCT/JP2018/015735 dated Jul. 24, 2018 (19 pages).
International Search Report including Written Opinion issued in the International Application No. PCT/JP2017/042522 dated Jan. 23, 2018 (14 pages).
Office Action issued in the U.S. Appl. No. 16/465,018, dated Jul. 10, 2020 (10 pages).
Extended European Search Report issued in corresponding European Application No. 18763621.2, dated Oct. 22, 2020 (10 pages).
Extended European Search Report issued in corresponding European Application No. 18788652.8, dated Oct. 23, 2020 (8 pages).
Office Action issued in U.S. Appl. No. 16/605,602, dated Dec. 8, 2020 (13 pages).
Extended European Search Report issued in corresponding European Application No. 18787662.8; dated Dec. 17, 2020 (6 pages).
Office Action issued in Russian Application No. 2019134976/04, dated Mar. 23, 2021 (11 pages).

* cited by examiner

CURABLE COMPOSITION FOR DENTAL USE, AND METHOD FOR PRODUCING SAME

CROSS-REFERENCE TO RELATED APPLICATIONS:

This application claims priority to Japanese Patent Application No. 2017-082024 filed on Apr. 18, 2017. The disclosure of this priority application is incorporated in its entirety in the present specification by reference.

TECHNICAL FIELD

The present invention relates to a dental curable composition, and a method for producing the same. More particularly, the invention relates to a dental curable composition that can have the external appearance color tone well-controlled without using a dye, a pigment, and the like and provides excellent convenience and esthetics, a dental filling restorative material formed from the composition, and methods for producing those.

BACKGROUND ART

Since dental curable compositions, particularly, dental filling restorative materials can impart color tones equivalent to the color tone of natural tooth color and are easily operable, dental filling restorative materials have been rapidly popularized as materials for restoring teeth that have been damaged by dental caries, fracture, and the like. In recent years, as a result of an enhancement of the mechanical strength and an enhancement of the adhesive force to teeth, dental filling restorative materials are also used for the restoration of anterior teeth as well as for molar teeth to which high occlusal pressure is exerted.

In recent years, in the field of dental filling restorative materials, there is an increasing demand not only for the recovery of occlusion but also for esthetic restoration of the appearance looking like natural teeth. There is a demand for a restorative material which can reproduce not only simple equivalent color tones but also the transparency and color tones at various restoration sites of teeth.

A natural tooth is formed from dentine and enamel, and the color tone (hue, chroma, and value) varies from site to site. For example, since an incisal part has a thin dentinal layer and is almost covered with enamel, the incisal part is highly transparent. In contrast, the tooth cervix is opaque because the dentinal layer is thick, and compared to an incisal part, the tooth cervix has high value (lightness or darkness of a color) and high chroma (vividness of color). That is, in a natural tooth, the chroma and value decrease in the direction from the tooth cervix where the dentinal layer is thick, toward the incisal part where the dentinal layer is thin. As such, since a tooth has different color tones at different sites, in order to obtain superior esthetic properties for tooth restoration, it is important to prepare a plurality of curable pastes having different color tones, and to select and use, from among those curable pastes, a curable paste having a color tone that is most suitable for the actual restored tooth and teeth adjacent thereto (hereinafter, also referred to as "periphery of the restored tooth") (see, for example, Non-Patent Document 1).

Such selection of color tone is carried out by a dentist, who uses a shade guide (color sample) that includes a collection of various cured product samples of prepared curable pastes, compares the respective color tones of the respective samples with the color tone of the periphery of the restored tooth that is checked by looking into the oral cavity, and selects a color tone that is felt to be closest to the color tone of the periphery of the restored tooth.

Furthermore, as long as it is not the case that the damage of the restored tooth is small with a shallow cavity, it is difficult to realize the adaptation of the color tone by means of filling of a single kind of curable paste. That is, if the cavity is deep (for example, Class 4 cavity), the color tone of a tooth is visually perceived in a state in which not only the color tone of the tooth flank part (enamel portion) but also the color tone of the deep part (dentinal portion) that shows through are combined to give a rich gradation. Therefore, a deep cavity is filled by laminating the curable pastes to be filled, by varying the color tone at a certain interval of depth, and thereby this subtle color tone is reproduced. Usually, this reproduction of color tone is carried out such that a plurality of curable pastes for dentinal restoration, which reproduce the color tones of the dentinal portion, is used and laminated from the deepest part (usually, lamination is continued while each layer is cured), and a curable paste for enamel restoration is laminated at the last surface layer (for example, see Non-Patent Documents 1 and 2).

As such, since there are individual differences and site differences in the color tone of teeth, arranging curable pastes that have their color tones strictly controlled in consideration of these differences, is substantially impossible in reality because a huge number of curable pastes are needed.

In addition, pigments, dyes, and the like have been conventionally used for the adjustment of the color tone of a curable paste, and a variety of color tones have been prepared by changing the mixing proportions of pigments, dyes, and the like having different color tones. However, the coloration by such pigments and dyes tends to deteriorate over years, causing decoloration or discoloration. In dental filling restorative materials, a phenomenon has frequently occurred, in which the material exhibits high color tone adaptability immediately after restoration but undergoes discoloration with a lapse of time after the restoration, and the external appearance of the restored site does not match that of a natural tooth.

In this regard, as a technology of coloring without using pigments, dyes, and the like, utilization of light interference is known in the field of interior construction materials or the field of recording materials (see, for example, Patent Documents 1 and 2). Coloration achieved by utilizing light interference has an advantage that the phenomenon of decoloration or discoloration observed in the case of using a pigment, a dye, and the like does not occur.

Patent Document 1: Japanese Unexamined Patent Application, Publication No. 2004-276492

Patent Document 2: Japanese Unexamined Patent Application, Publication No. 2001-239661

Non-Patent Document 1: MATSUMURA, Hideo and TAGAMI, Junji, rev., "Adhesion Yearbook 2006", 1st Edition, Quintessence Publishing Co., Ltd., published in August, 2006, pp. 129-137

Non-Patent Document 2: MIYAZAKI, Masashi, "Science & Technique of Composite Resin Restoration", $1^{st}$ Edition, Quintessence Publishing Co., Ltd., published in January, 2010, pp. 48-49

DISCLOSURE OF THE INVENTION

Problems to be Solved by the Invention

Restoration using a curable composition that utilizes colored light brought by interference of light (hereinafter, also referred to as "interfering light") is advantageous because there is no phenomenon of decoloration or discoloration that is seen in the case of using a colorant substance such as a pigment. However, for this restoration, there is a problem that a plurality of curable compositions needs to be prepared in order to adapt to the color tone of a natural tooth having shades in accordance with individual differences or different sites of restoration.

Therefore, an object of the present invention is to provide a dental curable composition, with which it is not necessary to prepare a plurality of curable compositions having different color tones, the workability for the restoration of a cavity is satisfactory, and a restoration resulting in an external appearance of a cured product to be formed, which matches natural teeth is enabled, while matching with natural teeth is sustained; a dental filling restorative material formed from the composition; and methods for producing those.

Means for Solving the Problems

In view of the above-described problems, the inventors of the present invention have continued a thorough investigation. As a result, the inventors found that the above-described problems can be solved by mixing two kinds of spherical fillers having particular particle diameters and particle size distributions, and adjusting the refractive indices of the spherical fillers to be larger than the refractive index of a polymer of a polymerizable monomer. Thus, the inventors completed the present invention.

That is, the method for producing a dental curable composition of the present invention includes mixing a polymerizable monomer (A); a spherical filler (B) having an average primary particle diameter within the range of from 230 nm to 290 nm; a spherical filler (C) having an average primary particle diameter within the range of from 100 nm to 500 nm and having an average primary particle diameter different from that of the spherical filler (B); and a polymerization initiator (D), in which 90% or more in number of the individual particles constituting the spherical filler (B) and the spherical filler (C) are present in a range of ±5% from the average primary particle diameter, and the polymerizable monomer (A), the spherical filler (B), and the spherical filler (C) satisfy requirement (X1) represented by the following formulae (1) and (2):

$$nP<nF_B \quad (1)$$

in formula (1), nP represents a refractive index at 25° C. of a polymer obtained by polymerizing the polymerizable monomer (A); and $nF_B$ represents a refractive index at 25° C. of the spherical filler (B), $$nP<nF_C \quad (2)$$

in formula (2), nP represents a refractive index at 25° C. of a polymer obtained by polymerizing the polymerizable monomer (A); and $nF_C$ represents a refractive index at 25° C. of the spherical filler (C).

The dental curable composition may be a dental filling restorative material. In this case, according to the method for producing a dental curable composition of the present invention, a dental filling restorative material can be produced.

Furthermore, the dental curable composition of the present invention includes a polymerizable monomer (A); a spherical filler (B) having an average primary particle diameter within a range of from 230 nm to 290 nm; a spherical filler (C) having an average primary particle diameter within a range of from 100 nm to 500 nm and having an average primary particle diameter different from that of the spherical filler (B); and a polymerization initiator (D), in which 90% or more in number of the individual particles constituting each of the spherical filler (B) and the spherical filler (C) are present in a range of ±5% from the average primary particle diameter, and the polymerizable monomer (A), the spherical filler (B), and the spherical filler (C) satisfy requirement (X1) represented by the following formulae (1) and (2):

$$nP<nF_B \quad (1)$$

in formula (1), nP represents a refractive index at 25° C. of a polymer obtained by polymerizing the polymerizable monomer (A); and $nF_B$ represents a refractive index at 25° C. of the spherical filler (B), $$nP<nF_C \quad (2)$$

in formula (2), nP represents a refractive index at 25° C. of a polymer obtained by polymerizing the polymerizable monomer (A); and $nF_C$ represents a refractive index at 25° C. of the spherical filler (C).

Furthermore, the dental filling restorative material of the present invention is formed from the dental curable composition of the present invention.

Effects of the Invention

The dental curable composition of the present invention exhibits color development conforming to the color tones of natural teeth that vary depending on the individual differences or the sites of restoration, and therefore, a restoration resulting in an external appearance of a cured product that matches the color tones of natural teeth can be carried out conveniently without preparing a plurality of curable compositions having different color tones. Furthermore, since the dental curable composition of the present invention utilizes interfering light, the curable composition does not undergo decoloration and discoloration and enables a restoration by which matching of a cured product to be formed and natural teeth is sustained. In addition, by changing the mixing ratio of the two kinds of spherical fillers to be incorporated, a dental curable composition having a colored light induced by interference of light adjusted can be obtained, and a restoration that matches natural teeth having a wider variety of color tones is enabled. As such, the dental curable composition of the present invention can be suitably used as a dental filling restorative material. Furthermore, according to the method for producing a dental curable composition of the present invention, a dental curable composition that is suitable as a dental filling restorative material can be produced.

PREFERRED MODE FOR CARRYING OUT THE INVENTION

[Dental Curable Composition and Dental Filling Restorative Material]

The dental curable composition of the present invention includes a polymerizable monomer (A), a spherical filler (B) having an average primary particle diameter within a range of from 230 nm to 290 nm, a spherical filler (C) having an average primary particle diameter within a range of from 100 nm to 500 nm and having an average primary particle diameter different from that of the spherical filler (B), and a polymerization initiator (D).

In order to achieve convenience of the operability for restoration of a cavity and sustainment of excellent esthetics and matching with natural teeth having a wide variety of color tones, the most significant feature of the present invention is that a spherical filler (B) and a spherical filler (C) having narrow particle size distributions are used, as well as that the polymerizable monomer (A), the spherical filler (B), and the spherical filler (C) are selected such that the relationship of the refractive indices satisfies requirement (X1) represented by the following formulae (1) and (2):

$$nP<nF_B \qquad (1)$$

in formula (1), nP represents a refractive index at 25° C. of a polymer obtained by polymerizing the polymerizable monomer (A); and $nF_B$ represents a refractive index at 25° C. of the spherical filler (B), $$nP<nF_C \qquad (2)$$

in formula (2), nP represents a refractive index at 25° C. of a polymer obtained by polymerizing the polymerizable monomer (A); and $nF_C$ represents a refractive index at 25° C. of the spherical filler (C).

As the conditions described above are all satisfied, a colored light induced by interference of light can be clearly identified even without using a dye, a pigment, or the like, and a dental curable composition that enables a restoration close to natural teeth and has satisfactory color tone adaptability, particularly a dental curable composition that is useful as a dental filling restorative material, can be obtained.

The spherical filler (B) has an average primary particle diameter within the range of 230 nm to 290 nm, and 90% or more in number of the individual particles constituting this filler are present in the range of ±5% from the average primary particle diameter. The spherical filler (C) has an average primary particle diameter within the range of 100 nm to 500 nm, and 90% or more in number of the individual particles constituting this filler are present in the range of ±5% from the average primary particle diameter. Meanwhile, the relationship between the particle sizes of the spherical filler (B) and the spherical filler (C) and the phenomenon of interference of light is considered to conform to the Bragg's diffraction conditions.

There are individual differences in the color tone of natural teeth, and the color tone may vary depending on the site to be restored; however, the dental curable composition of the present invention that utilizes the phenomenon of light interference can cope with various color tones. Specifically, in a case in which the chromaticity (hue and chroma) of a foundation tooth is high, external light such as radiated light is absorbed by a background having high chromaticity, and light other than the colored light (interfering light) produced from the dental curable composition that utilizes the phenomenon of light interference is suppressed. Therefore, a colored light can be observed. On the other hand, in a case in which the chromaticity of the foundation tooth is low, since external light such as radiated light is scattered and reflected by a background having low chromaticity, and the scattered and reflected light is stronger than the colored light (interfering light) produced from the dental curable composition that utilizes the phenomenon of light interference, the colored light is canceled and becomes weak.

Therefore, since strong colored light is produced in a natural tooth having high chromaticity, and weak colored light is produced in a natural tooth having low chromaticity, wide color tone adaptability can be exhibited with one kind of paste. As such, it is difficult to achieve the technology of matching the color tone of a natural tooth using one kind of paste irrespective of the level of chromaticity, in the case of a paste that is produced by mixing of coloring substances such as pigments.

The dental curable composition of the present invention has a feature that a colored light corresponding to the average primary particle diameter of the spherical filler (B) and the average primary particle diameter of the spherical filler (C) is produced by an interference phenomenon. Whether this colored light is produced or not is verified by measuring the spectral reflectance characteristics using a color difference meter under the conditions of making measurement on both a black background and a white background. On a black background (backing having a value of 1 according to the Munsell Color System), in a case in which the above-mentioned conditions are satisfied, a characteristic visible spectrum corresponding to the colored light is clearly identified; however, on a white background (backing having a value of 9.5 according to the Munsell Color System), a substantially uniform reflectance is exhibited over substantially the entire range of the visible spectrum (380 nm to 780 nm), and a particular reflection visible spectrum is not identifiable, while the light is substantially colorless. This is speculated to be because, on a black background, external light (for example, C light source or D65 light source) is absorbed or blocked, and a colored light induced by interference is emphasized; whereas on a white background, since scattered and reflected light of external light is strong, a colored light induced by interference is not easily observed.

In order to exhibit the effects of the present invention, it is important that with regard to the polymerizable monomer (A), the spherical filler (B), and the spherical filler (C), the relationship of refractive indices satisfies requirement (X1) represented by the following formulae (1) and (2).

$$nP<nF_B \qquad (1)$$

$$nP<nF_C \qquad (2)$$

As shown in formula (1), the dental curable composition of the present invention is such that the relationship between the refractive index nP at 25° C. of a polymer of the polymerizable monomer (A) and the refractive index $nF_B$ at 25° C. of the spherical filler (B) is $nP<nF_B$. Furthermore, as shown in formula (2), the relationship between the refractive index nP at 25° C. of a polymer of the polymerizable monomer (A) and the refractive index $nF_C$ at 25° C. of the spherical filler (C) is $nP<nF_C$. In a case in which the refractive index nFB of the spherical filler (B) and the refractive index $nF_C$ of the spherical filler (C) are high, and the refractive index nP of a polymer of the polymerizable monomer (A) is low, interfering light conforming to the Bragg's diffraction conditions is strongly exhibited in a cured product of the dental curable composition. However, in an opposite case, light having a short wavelength is more easily subjected to interference, and a colored light thus obtainable has a shorter wavelength and acquires a bluish tinge. Thus, the color tone adaptability is likely to become defective.

In order to exhibit the effects of the present invention, it is important that the average primary particle diameter of the spherical filler (B) is within the range of 230 nm to 290 nm. Generally, natural teeth have a yellow tinge or a reddish milky white color. In a case in which a spherical filler having an average primary particle diameter within the range of 230 nm to 290 nm is used, a colored light thus obtainable is yellow to red in color, and a restoration that matches well with teeth can be achieved by mixing the present components.

Furthermore, in order to exhibit the effects of the present invention, it is important that the average primary particle diameter of the spherical filler (C) is within the range of 100 nm to 500 nm, and the average primary particle diameter is an average primary particle diameter different from that of the spherical filler (B). When the particle diameter is within the range of the particle diameter described above, colored lights induced by interference of light, which are dependent on the respective particle diameters of the spherical filler (B) and the spherical filler (C), are exhibited without canceling each other. Furthermore, adjustment of the colored light is made possible by changing the mixing ratio of the two spherical fillers.

Hereinafter, various components of the dental curable composition of the present invention will be described.

<Polymerizable Monomer (A)>

Regarding the polymerizable monomer (A), any known polymerizable monomer can be used without any particular limitations. In view of dental applications, from the viewpoint of the rate of polymerization, a radical polymerizable or cationic polymerizable monomer is preferred. A particularly preferred radical polymerizable monomer is a (meth) acrylic compound. Examples of the (meth)acrylic compound include (meth)acrylates listed below. Furthermore, particularly preferred examples of the cationic polymerizable monomer include epoxies and oxetanes.

Generally, examples of (meth)acrylates as the (meth) acrylic compounds that are suitably used, include compounds shown in the following (I) to (III).

(I) Bifunctional Polymerizable Monomer
(i) Aromatic Compound-Based Monomer
2,2-bis(methacryloyloxyphenyl)propane,
2,2-bis[(3-methacryloyloxy-2-hydroxypropyloxy)phenyl] propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane,
2(4-methacryloyloxydiethoxyphenyl)-2-(4-methacryloyloxytriethoxyphenyl)propane,
2(4-methacryloyloxydipropoxyphenyl)-2-(4-methacryloyloxytriethoxyphenyl)propane,
2,2-bis(4-methacryloyloxypropoxyphenyl)propane,
2,2-bis(4-methacryloyloxyisopropoxyphenyl)propane, and the like,
and acrylates corresponding to these methacrylates;
diadducts obtainable from addition of vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds having an aromatic group, such as methylbenzene diisocyanate and 4,4'-diphenylmethane diisocyanate, and the like.

(ii) Aliphatic Compound-Based Monomer
ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-hexanediol dimethacrylate, and the like,
and acrylates corresponding to these methacrylates;
diadducts obtainable from addition products of vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds such as hexamethylene diisocyanate, trimethylhexamethylene diisocyanate, methylcyclohexane diisocyanate, isophorone diisocyanate, and methylenebis(4-cyclohexyl isocyanate), for example, 1,6-bis(methacrylethyloxycarbonylamino)trimethylhexane;
1,2-bis(3-methacryloyloxy-2-hydroxypropoxy)ethyl, and the like.

(II) Trifunctional Polymerizable Monomer
trimethylolpropane trimethacrylate,
trimethylolethane trimethacrylate,
pentaerythritol trimethacrylate,
trimethylolmethane trimethacrylate, and the like,
and acrylates corresponding to these methacrylates, and the like.

(III) Tetrafunctional Polymerizable Monomer
pentaerythritol tetramethacrylate,
pentaerythritol tetraacrylate;
diadducts obtainable from addition products of diisocyanate compounds such as methylbenzene diisocyanate, methylcyclohexane diisocyanate, isophorone diisocyanate, hexamethylene diisocyanate, trimethylhexamethylene diisocyanate, methylenebis(4-cyclohexyl isocyanate), 4,4-diphenylmethane diisocyanate, and tolylene-2,4-diisocyanate, and glycidol dimethacrylate, and the like.

Regarding these polyfunctional (meth)acrylate-based polymerizable monomers, a plurality of kinds of compounds may be used in combination, if necessary.

Furthermore, if necessary, monofunctional (meth)acrylate-based polymerizable monomers, including methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates, and polymerizable monomers other than the above-described (meth)acrylate-based polymerizable monomers, may also be used.

According to the present invention, as the polymerizable monomer (A), generally, a plurality of kinds of polymerizable monomers is used for the purpose of regulation of the physical properties (mechanical characteristics and adhesiveness to the tooth substance) of the cured product; however, at this time, it is desirable to set the types and amounts of the polymerizable monomers such that the refractive index at 25° C. of the polymerizable monomer (A) falls within the range of 1.38 to 1.55. That is, by setting the refractive index to the range of 1.38 to 1.55, the refractive index nP of a polymer obtained from the polymerizable monomer (A) can be set to the range of approximately 1.40 to 1.57, and thus it is easy to satisfy the requirement (X1). Meanwhile, in a case in which a plurality of kinds of polymerizable monomers is used as the polymerizable monomer (A), it is desirable that the refractive index of a mixture produced by mixing a plurality of kinds of polymerizable monomers falls in the range described above, and the individual polymerizable monomers may not necessarily fall in the range described above.

Meanwhile, the refractive index of polymerizable monomer or a cured product of the polymerizable monomer can be determined using an Abbe refractometer at 25° C.

<Spherical Filler (B) and Spherical Filler (C)>

A dental curable composition contains various filler materials such as an inorganic powder and an organic powder; however, in the dental curable composition of the present invention, a spherical filler (B) having an average primary particle diameter within the range of 230 nm to 290 nm and a spherical filler (C) having an average primary particle diameter within the range of 100 nm to 500 nm are incorporated for the purpose of exhibiting colored light induced by interference. A feature of the dental curable composition of the present invention is that the spherical filler (B) and the spherical filler (C) are spherical in shape, 90% or more in number of the individual particles constituting each of the spherical filler (B) and the spherical filler (C) are present in the range of ±5% from the average primary particle diameter, and the particle size distributions are narrow. Colored light induced by interference is produced when constituent particles accumulate regularly. Therefore, the spherical filler (B) and spherical filler (C) that constitute the present invention, which have a spherical shape and a narrow particle size distribution, produce colored light induced by interference. On the other hand, in the case of irregularly shaped particles produced by pulverization or the like, since the particle size distribution is broad, and the shape is also non-uniform, the particles do not accumulate regularly, and colored light is not produced.

With regard to the spherical filler (B) and the spherical filler (C), it is important that 90% (number of particles) or more of the individual particles constituting each of the fillers are present in the range of ±5% from the average primary particle diameter. That is, the spherical filler (B) and the spherical filler (C) are each independently composed of a plurality of primary particles, and 90% of primary particles in the total number of primary particles are present in the range of ±5% from the average particle diameter of the plurality of primary particles. This proportion is preferably 91% or more, and more preferably 93% or more.

Exhibition of colored light induced by diffraction and interference of light is achieved as diffraction and interference occur according to the Bragg's conditions, and light having a particular wavelength is emphasized. Thus, when particles having the above-mentioned particle diameters are incorporated, a cured product of the dental curable composition exhibits colored light according to the particle diameters. Furthermore, in the present invention, a spherical filler (B) and a spherical filler (C) having different average primary particle diameters are used, and colored lights caused by diffraction and interference of light, which are dependent on the respective particle diameters of the fillers, are exhibited. The respective colored lights are mixed, and thus coloration as a cured product is exhibited.

In order to exhibit the effects of the present invention, it is important that the average primary particle diameter of the spherical filler (B) is within the range of 230 nm to 290 nm. Generally, natural teeth have a yellow tinge or a reddish milky white color. In a case in which a spherical filler having an average primary particle diameter within the range of 230 nm to 290 nm is used, the colored light thus obtainable is yellow to red in color, and by incorporating this component, restoration that matches well with teeth is enabled.

Furthermore, in order to exhibit the effects of the present invention, it is important that the average primary particle diameter of the spherical filler (C) is within the range of 100 nm to 500 nm, and the average primary particle diameter is an average primary particle diameter different from that of the spherical filler (B). In this case, the colored light based on the spherical filler (C) becomes bluish-yellowish-reddish. When the particle diameter is within the above-mentioned range of particle diameter, colored lights induced by interference of light, which are dependent on the respective particle diameters of the spherical filler (B) and the spherical filler (C), are exhibited without canceling each other. Furthermore, adjustment of the colored light is enabled by changing the mixing ratio of the two spherical fillers.

From the viewpoint of making the adjustment of the colored light easier, the difference between the average primary particle diameters of the spherical filler (B) and the spherical filler (C) is preferably 40 nm or more.

From the viewpoint of further increasing the effect of exhibiting a colored light induced by interference, the average primary particle diameter of the spherical filler (C) is suitably 120 nm to 400 nm, more suitably 200 nm to 350 nm, even more suitably 230 nm to 300 nm, and particularly suitably 230 nm to 290 nm. In a case in which a spherical filler having an average primary particle diameter of smaller than 100 nm, a phenomenon of interference of visible light originating from the spherical filler does not easily occur. On the other hand, in a case in which a spherical filler having an average primary particle diameter of larger than 500 nm is used, exhibition of the phenomenon of interference of light originating from the spherical filler can be expected; however, interfering light originating from the spherical filler (B) is not easily produced. Furthermore, in a case in which the dental curable composition of the present invention is used as a dental filling restorative material, problems such as sedimentation of the spherical fillers and deterioration of abradability and abrasion resistance occur, which is not preferable.

The dental curable composition of the present invention exhibits various colored lights according to the particle diameters of the spherical filler (B) and the spherical filler (C). In a case in which a spherical filler having an average primary particle diameter within the range of 230 nm to 260 nm is used, the colored light thus obtainable is yellowish, and in a case in which a spherical filler having an average primary particle diameter within the range of 260 nm to 350 nm is used, the colored light thus obtainable is reddish. That is, in a case in which a spherical filler having an average primary particle diameter within the range of 230 nm to 260 nm is used as the spherical filler (B), and a spherical filler having an average primary particle diameter within the range of 260 nm to 350 nm is used as the spherical filler (C), a yellowish colored light and a reddish colored light are both exhibited, and the curable composition for dental use is useful for the restoration of teeth having a color in the class of B system (red-yellow) and A system (red-brown) according to Shade Guide "VITAPAN Classical", and is particularly useful for the restoration of a cavity formed over from the enamel to the dentine. Furthermore, adjustment of the colored light is enabled by changing the mixing ratio of the two. In a case in which a spherical filler having an average primary particle diameter within the range of 150 nm to 230 nm is used, the colored light thus obtainable is bluish. In a case in which a spherical filler having an average primary particle diameter within the range of 230 nm to 290 nm is used as the spherical filler (B), and a spherical filler having an average primary particle diameter within the range of 150 nm to 230 nm is used as the spherical filler (C), a blue colored light originating from the spherical filler (C) is exhibited in addition to a yellow to reddish colored light originating from the spherical filler (B), and matching with the incisal part of the enamel and matching with the teeth in the class of C system (gray) according to Shade Guide "VITAPAN Classical" can be imparted.

According to the present invention, the average primary particle diameters of the spherical filler (B) and the spherical filler (C) are determined by taking a photograph of the powders with a scanning electron microscope, selecting thirty or more particles observed within a unit viewing field of the photograph, determining the respective primary particle diameters (maximum diameters), and calculating the average primary particle diameters by the following calculation formula.

$$\bar{x} = \frac{\sum_{i=1}^{n} x_i}{n} \quad \text{(Number average)}$$

($n$: number of particles, $x_j$: primary particle diameter (maximum diameter) of i-th particle)

Here, the spherical shape of the spherical filler may be approximately spherical, and it is not necessarily essential to be a perfect true sphere. When a photograph of particles is taken by scanning electron microscopy, for the maximum diameter for each of the particles (thirty or more particles) present within a unit viewing field of the photograph, the average uniformity is obtained by dividing the particle diameter in a direction orthogonally intersecting the maximum diameter by the maximum diameter, the average uniformity is desirably 0.6 or higher, and more preferably 0.8 or higher.

As described above, colored light induced by interference is exhibited with high color tone adaptability to natural teeth in a case in which requirement (X1) represented by the following formulae (1) and (2) is satisfied:

$$nP < nF_B \quad (1)$$

in formula (1), $nP$ represents the refractive index at 25° C. of a polymer obtained by polymerizing the polymerizable monomer (A); and $nF_B$ represents the refractive index at 25° C. of the spherical filler (B), $$nP < nF_C \quad (2)$$

in formula (2), $nP$ represents the refractive index at 25° C. of a polymer obtained by polymerizing the polymerizable monomer (A); and $nF_C$ represents the refractive index at 25° C. of the spherical filler (C).

That is, the refractive indices ($nF_B$ and $nF_C$) of the spherical filler (B) and the spherical filler (C) are in a state of being higher than the refractive index $nP$ of a polymer obtained by polymerizing the polymerizable monomer (A). The refractive index difference from the refractive index $nP$ of a polymer obtained by polymerizing the polymerizable monomer (A) is preferably 0.001 or more, more preferably 0.002 or more, and even more preferably 0.005 or more. With regard to the refractive index, since it is more clearly exhibited in a case in which transparency of the cured product is high, the refractive index difference between the refractive indices of the spherical filler (B) and the spherical filler (C) and the refractive index of a polymer of the polymerizable monomer (A) is 0.1 or less, and more preferably 0.05 or less, and it is preferable to select and use components that do not impair transparency as far as possible.

Regarding the spherical filler (B) and the spherical filler (C), fillers that are used as the same component of dental curable compositions in the field of dentistry can be used without limitations. Specific examples include inorganic powders such as amorphous silica, silica-titanium group oxide-based composite oxide particles (silica-zirconia, silica-titania, and the like), quartz, alumina, barium glass, zirconia, titania, lanthanoids, and colloidal silica. Furthermore, organic powders or organic-inorganic composite powders can also be used.

Among these, from the viewpoint that the adjustment of the refractive index of the filler is easy, silica-titanium group oxide-based composite oxide particles are preferred.

The silica-titanium group oxide-based composite oxide particles according to the present invention are composite oxides of silica and titanium group (elements of Group 4 in the Periodic Table of Elements) oxides, and examples include silica-titania, silica-zirconia, and silica-titania-zirconia. Among these, from the viewpoint that the refractive index of the filler can be adjusted and high opacity to X-rays can be imparted, silica-zirconia is preferred. The composite ratio is not particularly limited; however, from the viewpoint of imparting sufficient opacity to X-rays and adjusting the refractive index to the suitable range that will be described below, it is preferable that the content of silica is 70 mol % to 95 mol %, and the content of the titanium group oxide is 5 mol % to 30 mol %. In the case of silica-zirconia, the refractive index can be freely changed by changing the respective composite ratios as such.

Meanwhile, in these silica-titanium group oxide-based composite oxide particles, compounding of a metal oxide other than silica and a titanium group oxide is also allowed, as long as the amount is small. Specifically, an alkali metal oxide such as sodium oxide or lithium oxide may also be incorporated in an amount of 10 mol % or less.

The method for producing the silica-titanium group oxide-based composite oxide particles is not particularly limited; however, in order to obtain the specific spherical filler of the present invention, for example, a so-called sol-gel method of adding a mixed solution including a hydrolyzable organosilicon compound and a hydrolyzable organotitanium group metal compound to an alkaline solvent, performing hydrolysis, and precipitating a reaction product, is suitably employed.

These silica-titanium group oxide-based composite oxide particles may be surface-treated with a silane coupling agent. Through a surface treatment using a silane coupling agent, excellent interfacial strength between the composite oxide particles and a cured part of the polymerizable monomer (A) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be decided after the mechanical properties and the like of the dental curable composition thus obtainable are checked in advance by experiments. An example of a suitable range is the range of 0.1 parts by mass to 15 parts by mass with respect to 100 parts by mass of the particles.

The spherical filler (B) and the spherical filler (C) may also be incorporated as organic-inorganic composite fillers produced by mixing with the polymerizable monomer (A) and the like and polymerizing the mixture. At this time, the spherical filler (B) and the spherical filler (C) may be incorporate as different organic-inorganic composite fillers, or may be incorporated as an organic-inorganic composite filler produced by mixing the spherical filler (B) and the spherical filler (C).

The method for producing an organic-inorganic composite filler is not particularly limited, and for example, a general production method of mixing predetermined amounts of the respective components of the spherical filler (B) and/or the spherical filler (C), the polymerizable monomer, and the polymerization initiator, polymerizing the mixture by a method such as heating or light irradiation, and then pulverizing the polymerization product, can be employed. Alternatively, the production method described in WO 2011/115007 or WO 2013/039169 may also be employed. In this production method, inorganic aggregate particles formed by aggregation of the spherical inorganic filler (b2) are immersed in a polymerizable monomer solvent including a polymerizable monomer, a polymerization initiator, and an organic solvent, subsequently the organic solvent is removed, and the polymerizable monomer is polymerized and cured by a method such as heating or light irradiation. According to the production method described in WO 2011/115007 or WO 2013/039169, an organic-inorganic composite filler in which inorganic primary particles cover the surface of the inorganic primary particles of the aggregated inorganic aggregate particles, an organic resin phase that binds the respective inorganic primary particles is included, and aggregation gaps are formed between the organic resin phase that covers the surface of the respective inorganic primary particles are formed, can be obtained.

The total incorporation amount of the spherical filler (B) and the spherical filler (C) according to the present invention is preferably 100 parts by mass to 1,500 parts by mass with respect to 100 parts by mass of the polymerizable monomer (A). When the spherical filler (B) and the spherical filler (C) are each incorporated in an amount of 50 parts by mass or more, colored light induced by interference is satisfactorily exhibited, which is preferable. Furthermore, as the spherical filler (B) and the spherical filler (C), in a case in which fillers each having a refractive index difference of more than 0.1 with a polymer of the polymerizable monomer (A) are used, there is a risk that transparency of the cured product may be decreased, and the effect of exhibiting colored light may not be sufficiently exhibited. In consideration of these, the total incorporation amount of the spherical filler (B) and the spherical filler (C) is more preferably 150 parts by mass to 1,500 parts by mass with respect to 100 parts by mass of the polymerizable monomer (A).

Among the spherical filler (B) and the spherical filler (C), the refractive index of a silica-titanium group oxide-based composite oxide, for which adjustment of the refractive index is easy, falls in the range of about 1.45 to 1.58 depending on the content of the silica portion. By having the refractive index of the polymerizable monomer (A) set to the range described above (1.38 to 1.55), the spherical filler (B) and the spherical filler (C) can be easily selected so as to satisfy the above-mentioned requirement (X1). That is, a silica-titanium group oxide-based composite oxide (for example, silica-titania, or silica-zirconia) containing an adequate amount of silica portion may be used.

<Polymerization Initiator (D)>

A polymerization initiator is incorporated for the purpose of polymerizing and curing the present composition, and any known polymerization initiator is used without any particular limitations.

Above all, in a dental direct filling restoration application in which curing is frequently achieved within the oral cavity, the composition using a photopolymerization initiator or a chemical polymerization initiator is preferred, and from the viewpoint that a mixing operation is unnecessary, and the operation is convenient, a photopolymerization initiator is more preferred.

Regarding the polymerization initiator used for photopolymerization, benzoin alkyl ethers such as benzoin methyl ether, benzoin ethyl ether, and benzoin isopropyl ether; benzyl ketals such as benzyl dimethyl ketal and benzyl diethyl ketal; benzophenones such as benzophenone, 4,4'-dimethylbenzophenone, and 4-methacryloxybenzophenone; α-diketones such as diacetyl, 2,3-pentadionebenzyl, camphor-quinone, 9,10-phenanthraquinone, and 9,10-anthraquinone; thioxanthone compounds such as 2,4-diethoxythioxanthone, 2-chlorothioxanthone, and methylthioxanthone; and bisacylphosphine oxides such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis(2,4,6-trimethylbenzoyl)-phenylphosphine oxide, and the like can be used.

Meanwhile, as the photopolymerization initiator, a reducing agent is frequently added, and examples thereof include tertiary amines such as 2-(dimethylamino)ethyl methacrylate, ethyl 4-dimethylaminobenzoate, and N-methyldiethanolamine; aldehydes such as lauryl aldehyde, dimethylaminobenzaldehyde, and terephthalic aldehyde; and sulfur-containing compounds such as 2-mercaptobenzoxazole, 1-decanethiol, thiosalicylic acid, and thiobenzoic acid.

Furthermore, cases of using a composition by adding a photoacid generator, in addition to the photopolymerization initiator and the reducing compound, may be frequently seen. Examples of such a photoacid generator include a diaryliodonium salt-based compound, a sulfonium salt-based compound, a sulfonic acid ester compound, a halomethyl-substituted-S-triazine derivative, and a pyridinium salt-based compound.

According to the present invention, changes in the color tone caused by silica-titanium group oxide-based composite oxide particles occur noticeably in a case in which an amine compound is included as a reducing agent for the polymerization initiator. Therefore, in the present invention, it is particularly effective to use a polymerization initiator containing an amine as a component as such.

These polymerization initiators may be used singly, or two or more kinds thereof may be used as mixtures. Regarding the incorporation amount of the polymerization initiator, an effective amount may be selected according to the purpose; however, the polymerization initiator is usually used at a proportion of 0.01 to 10 parts by mass, and preferably at a proportion of 0.1 to 5 parts by mass, with respect to 100 parts by mass of the polymerizable monomer (A).

<Other Additives>

In the dental curable composition of the present invention, other known additives can be incorporated in addition to the components (A) to (D) described above, to the extent that the effects are not impaired. Specific examples include a polymerization inhibitor and an ultraviolet absorber. Furthermore, for the purpose of viscosity adjustment and the like, a filler having a particle diameter that is sufficiently smaller than the wavelengths of light and does not easily affect the color tone or transparency may also be incorporated.

As described above in the present invention, even if a coloring substance such as a pigment is not used, restoration with satisfactory color tone adaptability to natural teeth is enabled with a single paste (dental curable composition). Therefore, an embodiment in which a pigment having a risk of being discolored with time is not incorporated is preferred. However, according to the present invention, incorporation of a pigment is not to be denied per se, and a pigment may be incorporated to the extent that does not obstruct the colored light induced by interference of spherical fillers. Specifically, a pigment in an amount of about 0.0005 parts by mass to 0.5 parts by mass, and preferably about 0.001 parts by mass to 0.3 parts by mass, with respect to 100 parts by mass of the polymerizable monomer, may be incorporated.

The dental curable composition of the present invention is particularly suitably used as a dental filling restorative material represented by a photocurable composite resin as described above; however, the usage is not limited there, and the dental curable composition can also be suitably used for other applications. Examples of the use thereof include dental cement and a restorative material for abutment construction.

[Methods for Producing Dental Curable Composition and Dental Filling Restorative Material]

The dental curable composition and the dental filling restorative material of the present invention can be produced by mixing a polymerizable monomer (A), a spherical filler (B), a spherical filler (C), a polymerization initiator (D), and other additives as necessary. Suitable examples and incorporation amounts of the respective components are as described above, and therefore, detailed explanation will not be repeated.

The mixing order of the respective components is not particularly limited. For example, a method of mixing a polymerizable monomer (A) and a polymerization initiator (D), preparing a polymerizable monomer composition, subsequently slowly adding the polymerizable monomer composition to a spherical filler (B) and a spherical filler (C), kneading the mixture, and obtaining a uniform curable paste, may be mentioned. It is preferable that the curable paste thus obtained is degassed under reduced pressure to remove air bubbles.

EXAMPLES

Hereinafter, the present invention will be more specifically described by way of Examples; however, the present invention is not intended be limited to these Examples.

The methods for measuring various physical properties according to the present invention are as follows.

(1) Average Primary Particle Diameter of Spherical Filler

A photograph of a powder was taken with a scanning electron microscope (manufactured by Philips N.V., "XL-30S"), the number (30 or more particles) and the primary particle diameters (maximum diameters) of the particles observed within a unit viewing field of the photograph were measured, and the average primary particle diameter was calculated by the following formula based on the measured values.

$$\bar{x} = \frac{\sum_{i=1}^{n} x_i}{n} \text{ (Number average)}$$

(n: number of particles, $x_j$: primary particle diameter (maximum diameter) of i-th particle)

(2) Abundance Proportion of Average Particle-Sized Particles of Spherical Filler The number of particles that exceeded the range of ±5% from the average primary particle diameter obtained in the above section (1) was measured, and this number was divided by the number of particles (30 or more) observed within a unit viewing field of the photograph. The value thus obtained was subtracted from 1, and the resultant was multiplied by 100. Thus, the proportion of particles that were present in the range of 5% greater or less than the average primary particle diameter was calculated, and this was designated as the abundance proportion of the average particle-sized particles.

(3) Uniformity

A photograph of a powder was taken with a scanning electron microscope (manufactured by Philips N.V., "XL-30S"), and for each of the particles (thirty or more particles) present within a unit viewing field of the photograph, a value obtained by dividing the particle diameter in a direction orthogonally intersecting the maximum diameter, by the maximum diameter, was determined. The average of the values was designated as uniformity.

(4) Measurement of Refractive Index

<Refractive Index of Polymerizable Monomer (A)>

The refractive index of the polymerizable monomer (or a mixture of polymerizable monomers) used was measured in a constant temperature chamber at 25° C. using an Abbe refractometer (manufactured by Atago Co., Ltd.).

<Refractive Index nP of Polymer of Polymerizable Monomer (A)>

The refractive index of a polymer of the polymerizable monomer (or a mixture of polymerizable monomers) used was measured using a polymer polymerized under conditions almost the same as the polymerization conditions in a cavity, in a constant temperature chamber at 25° C. using an Abbe refractometer (manufactured by Atago Co., Ltd.).

That is, a uniform polymerizable monomer (or a mixture of polymerizable monomers) obtained by mixing 0.2% by mass of camphor-quinone, 0.3% by mass of ethyl N,N-dimethyl-p-benzoate, and 0.15% by mass of hydroquinone monomethyl ether was introduced into a mold having a hole having a size of 7 mmφ×0.5 mm, and a polyester film was pressure-welded on both surfaces. Subsequently, the polymerizable monomer was cured by irradiating the monomer with light for 30 seconds using a halogen type dental light irradiator (manufactured by Sybron Dental Specialties, Inc., "Demetron LC") at a quantity of light of 500 mW/cm², and then the cured product was removed from the mold. Thus, a polymer of the polymerizable monomer was produced. When the polymer was placed in an Abbe refractometer (manufactured by Atago Co., Ltd.), for the purpose of tightly adhering the polymer with the measuring surface, a solvent which does not dissolve the sample and having a refractive index higher than that of the sample (bromonaphthalene) was added dropwise to the sample, and the refractive index was measured.

<Refractive Indices of Spherical Filler and Irregularly Shaped Filler>

The refractive indices of a spherical filler and an irregularly shaped filler used were measured using an Abbe refractometer (manufactured by Atago Co., Ltd.) according to an immersion method.

That is, in a constant temperature chamber at 25° C., 1 g of a spherical filler or a surface-treated product thereof was dispersed in 50 mL of anhydrous toluene in a 100-mL sample bottle. While this dispersion liquid was stirred with a stirrer, 1-bromotoluene was added dropwise in small amounts, the refractive index of the dispersion liquid at the time point when the dispersion liquid became most transparent was measured, and the value thus obtained was designated as the refractive index of the spherical filler and an irregularly shaped filler.

(5) Evaluation of Colored Light by Visual Inspection

A paste of each of the dental curable compositions produced in Examples and Comparative Examples was introduced into a mold having a hole having a size of 7 mmϕ×1 mm, and a polyester film was pressure-welded on both surfaces. Both surfaces were cured by irradiating with light for 30 seconds with a visible light irradiator (manufactured by Tokuyama Corp., POWER LIGHT), and then the resultant was removed from the mold. The cured product was mounted on an adhesive surface of a black tape (carbon tape) that measured about 10 mm on each edge, and the color tone of colored light was checked by visual inspection.

(6) Wavelength of Colored Light

A paste of each of the dental curable compositions produced in Examples and Comparative Examples was introduced into a mold having a hole having a size of 7 mmϕ×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The spectral reflectance was measured using a color difference meter (manufactured by Tokyo Denshoku Co., Ltd., "TC-1800 MKII") on the black background color and on the white background color, and the maximum point of the reflectance on the black background color was designated as the wavelength of the colored light.

(7) Evaluation of Color Tone Adaptability

A model tooth for tooth restoration that reproduced an incisal part loss cavity (width 2 mm, depth 1 mm) of lower right No. 1, and a model tooth for tooth restoration that reproduced a Class I cavity (diameter 4 mm, depth 2 mm) of lower right No. 6 were used. The cavity was filled with a paste of a dental curable composition, the paste was cured and polished, and the color tone adaptability was checked by visual inspection. Meanwhile, as the model teeth for tooth restoration, a high-chromaticity model tooth of high hue and high chroma (corresponding to A4) and a low-chromaticity model tooth of low hue and low chroma (corresponding to A1) in the class of A system (red-brown) according to Shade Guide "VITAPAN Classical"; a high-chromaticity model tooth of high hue and high chroma (corresponding to B4) and a low-chromaticity model tooth of low hue and low chroma (corresponding to B1) in the class of B system (red-yellow) according to Shade Guide "VITAPAN Classical"; and a high-chromaticity model tooth of high hue and high chroma (corresponding to C4) and a low-chromaticity model tooth of low hue and low chroma (corresponding to C1) in the class of C system (gray) according to Shade Guide "VITAPAN Classical" were used.

—Evaluation Criteria—

A: The color tone of the restoration product highly matches with that of the model tooth for tooth restoration.
B: The color tone of the restoration product is similar to that of the model tooth for tooth restoration.
C: The color tone of the restoration product is similar to that of the model tooth for tooth restoration; however, adaptability is not satisfactory.
D: The color tone of the restoration product does not match with that of the model tooth for tooth restoration.

(8) Change in Color Tone Over Time

A paste of each of the dental curable compositions produced in Examples and Comparative Examples was introduced into a mold having a hole having a size of 7 mmϕ×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The cured product was stored in water at 37° C. for 4 months, and the color tone after the storage was measured using a color difference meter (manufactured by Tokyo Denshoku Co., Ltd., "TC-1800MKII"). The difference between the color tones before and after the storage is represented by $\Delta E^*$ in the CIELab.

$$\Delta E^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

Meanwhile, $L1^*$: psychometric lightness index of cured product after storage, $a1^*$ and $b1^*$: chroma indices of cured product after storage, $L2^*$: lightness index of cured product before storage, $a2^*$ and $b2^*$: chroma indices of cured product before storage, $\Delta E^*$: amount of change in color tone.

The polymerizable monomers, polymerization initiators, and the like used in Examples and Comparative Examples were as follows.

[Polymerizable Monomers]
  1,6-Bis(methacrylethyloxycarbonylamino)trimethylhexane (hereinafter, abbreviated to "UDMA")
  Triethylene glycol dimethacrylate (hereinafter, abbreviated to "3G")
  2,2-Bis[(3-methacryloyloxy-2-hydroxypropyloxy)phenyl]propane (hereinafter, abbreviated to "bis-GMA")

[Polymerization Initiator]
  Camphor-quinone (hereinafter, abbreviated to "CQ")
  Ethyl N,N-dimethyl-p-benzoate (hereinafter, abbreviated to "DMBE")

[Polymerization Inhibitor]
  Hydroquinone monomethyl ether (hereinafter, abbreviated to "HQME")

[Colorant]
  Titanium dioxide (white pigment)
  Pigment Yellow (yellow pigment)
  Pigment Red (red pigment)
  Pigment Blue (blue pigment)

[Preparation of Mixture of Polymerizable Monomers]

The polymerizable monomers shown in Table 1 were mixed, and polymerizable monomers M1 and M2 were produced. The values in the parentheses in Table 1 represent the mass ratio of the respective polymerizable monomers.

TABLE 1

| | | Refractive index | |
| --- | --- | --- | --- |
| | | Before curing | After curing |
| M1 | UDMA(60)/3G(40) | 1.474 | 1.509 |
| M2 | bis-GMA(50)/3G(50) | 1.506 | 1.540 |

[Production of Spherical Filler and Irregularly Shaped Filler]

A spherical filler was produced by the methods described in Japanese Unexamined Patent Application, Publication No. S58-110414, Japanese Unexamined Patent Application, Publication No. S58-156524, and the like. That is, a spherical filler was produced using a so-called sol-gel method of adding a mixed solution including a hydrolyzable organosilicon compound (tetraethyl silicate or the like) and a hydrolyzable organic titanium group metal compound (tetrabutyl zirconate, tetrabutyl titanate, or the like) into an ammoniacal alcohol (for example, methanol, ethanol, isopropyl alcohol, or isobutyl alcohol) solution having aqueous ammonia incorporated therein, performing hydrolysis, and precipitating out a reaction product.

An irregularly shaped filler was produced by the method described in Japanese Unexamined Patent Application, Publication No. H02-132102, Japanese Unexamined Patent Application, Publication No. H03-197311, or the like. That is, an irregularly shaped filler was produced using a method of dissolving an alkoxysilane compound in an organic solvent, adding water to this solution to perform partial hydrolysis, further adding thereto an alkoxide of another metal and an alkali metal compound to be compounded, thereby performing hydrolysis to produce a gel-like material, subsequently drying the gel-like material, subsequently pulverizing the dried product as necessary, and calcining the pulverization product.

The spherical filler and irregularly shaped filler used in Examples and Comparative Examples are shown in Table 2.

3 and Table 4. The values in the parentheses in Table 3 represent the incorporation amounts (unit: parts by mass) of the various components.

Comparative Examples 1 to 5

To 100 g of polymerizable monomer M1, 0.3% by mass of CQ, 1.0% by mass of DMBE, and 0.15% by mass of HQME were added and mixed, and a uniformly polymerizable monomer composition was prepared. Next, the various fillers indicated in Table 3 were weighed in a mortar, the above-mentioned polymerizable monomer composition was slowly added thereto under red light, and the mixture was sufficiently kneaded in the dark to obtain a uniform curable paste. Furthermore, this paste was degassed under reduced pressure to eliminate air bubbles, and thus a dental curable composition was produced. For the dental curable composition thus obtained, various physical properties were evaluated based on the above-described methods. The composition and results are shown in Table 3 and Table 4.

TABLE 2

| | Composition and shape of filler | | Average primary particle | | | Abundance of average particle-sized particles[1] |
|---|---|---|---|---|---|---|
| | Composition (mol %) | Shape | diameter nm | Refractive index | Uniformity | % |
| PF1 | $SiO_2/ZrO_2/Na_2O$ = 89.8/9.0/1.2 | Spherical | 230 | 1.515 | 0.90 | 92 |
| PF2 | $SiO_2/ZrO_2/Na_2O$ = 89.8/9.0/1.2 | Spherical | 280 | 1.515 | 0.88 | 95 |
| PF3 | $SiO_2/ZrO_2/Na_2O$ = 89.8/9.0/1.2 | Spherical | 178 | 1.515 | 0.91 | 91 |
| PF4 | $SiO_2/ZrO_2/Na_2O$ = 88.7/10.8/1.2 | Spherical | 282 | 1.522 | 0.81 | 93 |
| PF5 | $SiO_2/ZrO_2/Na_2O$ = 83.9/14.3/1.8 | Spherical | 286 | 1.542 | 0.80 | 91 |
| PF6 | $SiO_2/ZrO_2/Na_2O$ = 83.5/14.7/1.8 | Spherical | 230 | 1.544 | 0.90 | 90 |
| PF7 | $SiO_2/ZrO_2/Na_2O$ = 89.8/9.0/1.2 | Spherical | 80 | 1.515 | 0.95 | 92 |
| PF8 | $SiO_2/ZrO_2/Na_2O$ = 89.8/9.0/1.2 | Irregularly shaped | 500 | 1.515 | — | 50 |
| PF9 | $SiO_2/ZrO_2/Na_2O$ = 89.8/9.0/1.2 | Spherical | 280 | 1.515 | 0.85 | 87 |

[1] The abundance of average particle-sized particles is the proportion (%) of particles present in the range of ±5% from the average particle diameter.

Examples 1 to 9

To 100 g of polymerizable monomer M1 or M2, 0.3% by mass of CQ, 1.0% by mass of DMBE, and 0.15% by mass of HQME were added and mixed, and uniformly polymerizable monomer compositions were prepared. Next, the various spherical fillers indicated in Table 3 were weighed in a mortar, each of the above-mentioned polymerizable monomer compositions was slowly added thereto under red light, and the mixture was sufficiently kneaded in the dark to obtain a uniform curable paste. Furthermore, this paste was degassed under reduced pressure to eliminate air bubbles, and thus a dental curable composition was produced. For the dental curable composition thus obtained, various physical properties were evaluated based on the above-described methods. The compositions and results are shown in Table 3 and Table 4.

Comparative Example 6

To 100 g of polymerizable monomer M2, 0.3% by mass of CQ, 1.0% by mass of DMBE, and 0.15% by mass of HQME were added and mixed, and a uniformly polymerizable monomer composition was prepared. Next, the spherical filler indicated in Table 3 were weighed in a mortar, the above-mentioned polymerizable monomer composition was slowly added thereto under red light. Furthermore, 0.050 g of titanium dioxide (white pigment), 0.001 g of Pigment Yellow (yellow pigment), 0.0005 g of Pigment Red (red pigment), and 0.0002 g of Pigment Blue (blue pigment) were added to the mixture, and the mixture was sufficiently kneaded in the dark to obtain a uniform curable paste. Furthermore, this paste was degassed under reduced pressure to eliminate air bubbles, and thus a dental composite restorative material was produced. In an evaluation by visual inspection, the material had a color tone that matched A system of a high-chromaticity model tooth. Subsequently, various physical properties were evaluated based on the above-described methods. The composition and results are shown in Table 3 and Table 4.

TABLE 3

| | Polymerizable monomer (A) Type (Incorporation amount) | Spherical filler (B) | | | Spherical filler (C) | | | Evaluation of colored light by visual inspection | Colored light (nm) on white background | Change in color tone over time ΔE* |
|---|---|---|---|---|---|---|---|---|---|---|
| | | Type (Incorporation amount) | Colored light (nm) on black background | Spectral reflectance of colored light (%) | Type (Incorporation amount) | Colored light (nm) on black background | Spectral reflectance of colored light (%) | | | |
| Example 1 | M1 (100) | PF1 (75) | 603 | 13 | PF2 (75) | 758 | 13 | Orange | No maximum | 1.5 |
| Example 2 | M1 (100) | PF1 (100) | 603 | 14 | PF2 (50) | 758 | 11 | Orange | No maximum | 1.4 |
| Example 3 | M1 (100) | PF1 (50) | 603 | 11 | PF2 (100) | 758 | 14 | Orange | No maximum | 1.4 |
| Example 4 | M1 (100) | PF1 (100) | 603 | 13 | PF3 (50) | 485 | 12 | Yellow | No maximum | 1.6 |
| Example 5 | M1 (100) | PF1 (75) | 603 | 11 | PF3 (75) | 485 | 13 | Yellow-blue | No maximum | 1.6 |
| Example 6 | M1 (100) | PF1 (50) | 603 | 10 | PF3 (100) | 485 | 15 | Yellow-blue | No maximum | 1.4 |
| Example 7 | M1 (100) | PF1 (75) | 603 | 13 | PF4 (75) | 760 | 13 | Orange | No maximum | 1.2 |
| Example 8 | M1 (100) | PF2 (100) | 758 | 14 | PF3 (50) | 485 | 12 | Red-purple | No maximum | 2.1 |
| Example 9 | M2 (100) | PF6 (75) | 600 | 13 | PF5 (75) | 746 | 13 | Orange | No maximum | 1.2 |
| Comparative Example 1 | M1 (100) | PF1 (150) | 603 | 14 | — | — | — | Yellow | No maximum | 1.5 |
| Comparative Example 2 | M1 (100) | PF2 (150) | 758 | 14 | — | — | — | Red | No maximum | 1.4 |
| Comparative Example 3 | M1 (100) | — | — | — | PF7 (150) | 405 | 6 | None | No maximum | 1.6 |
| Comparative Example 4 | M1 (100) | — | — | — | PF8 (150) | No maximum | — | None | No maximum | 2 |
| Comparative Example 5 | M1 (100) | PF9 (150) | 741 | — | — | — | — | Pale red | No maximum | 2.1 |
| Comparative Example 6 | M2 (100) | PF1 (150) | — | — | — | — | — | — | — | 4.5 |

TABLE 4

| | Model tooth | Filling site | Color tone adaptability (Low-chromaticity model tooth) A system | Color tone adaptability (High-chromaticity model tooth) A system | Color tone adaptability (Low-chromaticity model tooth) B system | Color tone adaptability (High-chromaticity model tooth) B system | Color tone adaptability (Low-chromaticity model tooth) C system | Color tone adaptability (High-chromaticity model tooth) C system |
|---|---|---|---|---|---|---|---|---|
| Example 1 | Lower right No. 6 | Central part of occlusal surface | A | A | A | A | B | B |
| Example 2 | Lower right No. 6 | Central part of occlusal surface | A | A | A | A | B | B |
| Example 3 | Lower right No. 6 | Central part of occlusal surface | A | A | A | A | B | B |
| Example 4 | Lower right No. 6 | Central part of occlusal surface | B | B | A | A | A | A |
| Example 5 | Lower right No. 1 | Incisal part | B | B | A | A | A | A |
| Example 6 | Lower right No. 1 | Incisal part | A | A | A | A | A | A |
| Example 7 | Lower right No. 6 | Central part of occlusal surface | A | A | A | A | B | B |
| Example 8 | Lower right No. 6 | Central part of occlusal aurrface | A | A | B | B | A | A |
| Example 9 | Lower right No. 6 | Central part of occlusal surface | A | A | A | A | B | B |

TABLE 4-continued

|  | Model tooth | Filling site | Color tone adaptability (Low-chromaticity model tooth) A system | Color tone adaptability (High-chromaticity model tooth) A system | Color tone adaptability (Low-chromaticity model tooth) B system | Color tone adaptability (High-chromaticity model tooth) B system | Color tone adaptability (Low-chromaticity model tooth) C system | Color tone adaptability (High-chromaticity model tooth) C system |
|---|---|---|---|---|---|---|---|---|
| Comparative Example 1 | Lower right No. 6 | Central part of occlusal surface | B | B | A | A | B | B |
| Comparative Example 2 | Lower right No. 6 | Central part of occlusal surface | A | A | B | B | B | B |
| Comparative Example 3 | Lower right No. 6 | Central part of occlusal surface | D | D | D | D | D | D |
| Comparative Example 4 | Lower right No. 6 | Central part of occlusal surface | D | D | D | D | D | D |
| Comparative Example 5 | Lower right No. 6 | Central part of occlusal surface | C | C | C | C | C | C |
| Comparative Example 6 | Lower right No. 6 | Central part of occlusal surface | C | B | D | D | D | D |

As is understood from the results of Examples 1 to 9, it can be seen that when the requirement defined in the present invention is satisfied, the dental curable composition exhibits a colored light induced by interference of light on a black background and has satisfactory color tone adaptability, and the change over time in the color tone of the cured product thus obtainable is small.

Furthermore, as is understood from the results of Examples 1 to 3, it can be seen that by varying the mixing ratio of the spherical filler (B) and the spherical filler (C), a spectral reflectance of the colored light that corresponds to the mixing ratio of the spherical fillers on a black background is exhibited.

As is understood from the results of Examples 4 to 6, it can be seen that in a case in which a filler having an average primary particle diameter of 230 nm is used as the spherical filler (B) and a filler having an average primary particle diameter of 178 nm is used as the spherical filler (C), adaptability to B system (red-yellow) and C system (gray) according to Shade Guide "VITAPAN Classical", and to the incisal part is obtained. Furthermore, it can be seen that as the incorporation amount of the spherical filler (C) increases, the adaptability to C system and the incisal part is enhanced.

As is understood from the results of Comparative Examples 1 and 2, in a case in which the spherical filler (C) is not used, satisfactory color tone adaptability is exhibited toward any one of A system (red-brown) and B system (red-yellow) according to Shade Guide "VITAPAN Classical"; however, the color tone range exhibiting satisfactory color tone adaptability is narrower than that of Examples 1 to 9.

As is understood from the results of Comparative Examples 3 to 5, it can be seen that when the requirement defined in the present invention is not satisfied, the dental curable composition does not exhibit colored light on a black background (Comparative Example 3: the average primary particle diameter of the spherical filler is 80 nm, Comparative Example 4: the shape of the filler is irregular), has a weak colored light (Comparative Example 5: the abundance of the average particle-sized particles of the spherical filler is 87%), and has poor color tone adaptability.

As is understood from the results of Comparative Example 6, for a dental curable composition having the color tone adjusted (color tone matching A system of a high-chromaticity model tooth (corresponding to A4)) by adding pigments, the spectral reflectance was measured on a black background color and a white background color using a color difference meter (manufactured by Tokyo Denshoku Co., Ltd., "TC-1800MKII"), and it was observed that the dental curable composition exhibits spectral reflection characteristics according to the added pigments on both the black background color and the white background color. The color tone adaptability to a color tone that matched A system of a high-chromaticity model tooth (corresponding to A4) was satisfactory; however, the color tone adaptability to other model teeth was low. Furthermore, the change in color tone over time was large.

The invention claimed is:

1. A method for producing a dental curable composition, the method comprising mixing a polymerizable monomer (A); a spherical filler (B) having an average primary particle diameter within a range of 230 nm to 290 nm; a spherical filler (C) having an average primary particle diameter within a range of 100 nm to 500 nm, the spherical filler (C) having the average primary particle diameter different from that of the spherical filler (B); and a polymerization initiator (D), wherein
90% or more in number of individual particles constituting the spherical filler (B) and the spherical filler (C) are present in a range of ±5% from the average primary particle diameter, and
the polymerizable monomer (A), the spherical filler (B), and the spherical filler (C) satisfy requirement (X1) represented by the following formulae (1) and (2):

$$nP < nF_B \tag{1}$$

in formula (1), nP represents a refractive index at 25° C. of a polymer obtained by polymerizing the polymerizable monomer (A); and $nF_B$ represents a refractive index at 25° C. of the spherical filler (B), $$nP < nF_C \tag{2}$$

in formula (2), nP represents the refractive index at 25° C. of a polymer obtained by polymerizing the polymerizable monomer (A); and $nF_C$ represents a refractive index at 25° C. of the spherical filler (C);

the difference between the average primary particle diameters of the spherical filler (B) and the spherical filler (C) is 40 nm or more;

a mixing ratio of the spherical filler (B) and the spherical filler (C) is in the range from 1:2 to 2:1 on a mass basis; and when the dental curable composition is cured to form a cured product, the spherical filler (B) in the cured product exhibits yellow to red colored light and the spherical filler (C) exhibits bluish-yellowish-reddish colored light.

2. The method for producing a dental curable composition according to claim 1, wherein the spherical filler (B) and the spherical filler (C) are incorporated in a total amount of 100 parts by mass to 1,500 parts by mass with respect to 100 parts by mass of the polymerizable monomer (A).

3. The method for producing a dental curable composition according to claim 2, wherein the spherical filler (B) is incorporated in an amount of 50 parts by mass or more, and the spherical filler (C) is incorporated in an amount of 50 parts by mass or more, with respect to 100 parts by mass of the polymerizable monomer (A).

4. The method for producing a dental curable composition according to claim 1, wherein the spherical filler (C) has the average primary particle diameter within a range of 230 nm to 290 nm.

5. The method for producing a dental curable composition according to claim 1, wherein the polymerizable monomer (A) includes a plurality of (meth)acrylic compounds, and a refractive index at 25° C. of the polymerizable monomer (A) is within a range of 1.38 to 1.55.

6. The method for producing a dental curable composition according to claim 1, wherein the spherical filler (B) is spherical silica-titanium group oxide-based composite oxide particles, and a refractive index thereof at 25° C. is within a range of 1.45 to 1.58.

7. The method for producing a dental curable composition according to claim 1, wherein the dental curable composition is a dental filling restorative material.

8. A dental curable composition comprising a polymerizable monomer (A); a spherical filler (B) having an average primary particle diameter within a range of 230 nm to 290 nm; a spherical filler (C) having an average primary particle diameter within a range of 100 nm to 500 nm, the spherical filler (C) having the average primary particle diameter different from that of the spherical filler (B); and a polymerization initiator (D), wherein 90% or more in number of individual particles constituting the spherical filler (B) and the spherical filler (C) are present in a range of ±5% from the average primary particle diameter, and the polymerizable monomer (A), the spherical filler (B), and the spherical filler (C) satisfy requirement (X1) represented by the following formulae (1) and (2):

$$nP < nF_B \quad (1)$$

in formula (1), nP represents a refractive index at 25° C. of a polymer obtained by polymerizing the polymerizable monomer (A); and $nF_B$ represents a refractive index at 25° C. of the spherical filler (B), $$nP < nF_C \quad (2)$$

in formula (2), nP represents the refractive index at 25° C. of a polymer obtained by polymerizing the polymerizable monomer (A); and nFc represents a refractive index at 25° C. of the spherical filler (C);

the difference between the average primary particle diameters of the spherical filler (B) and the spherical filler (C) is 40 nm or more;

a mixing ratio of the spherical filler (B) and the spherical filler (C) is 1:2 to 2:1 on a mass basis; and when the dental curable composition is cured to form a cured product, the spherical filler (B) in the cured product exhibits yellow to red colored light and the spherical filler (C) exhibits bluish-yellowish-reddish colored light.

9. The dental curable composition according to claim 8, wherein the spherical filler (B) and the spherical filler (C) are incorporated in a total amount of 100 parts by mass to 1,500 parts by mass with respect to 100 parts by mass of the polymerizable monomer (A).

10. The dental curable composition according to claim 9, wherein the spherical filler (B) is incorporated in an amount of 50 parts by mass or more, and the spherical filler (C) is incorporated in an amount of 50 parts by mass or more, with respect to 100 parts by mass of the polymerizable monomer (A).

11. The dental curable composition according to claim 8, wherein the spherical filler (C) has the average primary particle diameter within a range of 230 nm to 290 nm.

12. The dental curable composition according to claim 8, wherein the polymerizable monomer (A) includes a plurality of (meth)acrylic compounds, and a refractive index at 25° C. of the polymerizable monomer (A) is within a range of 1.38 to 1.55.

13. The dental curable composition according to claim 8, wherein the spherical filler (B) is spherical silica-titanium group oxide-based composite oxide particles, and a refractive index thereof at 25° C. is within a range of 1.45 to 1.58.

14. A dental filling restorative material consisting of the dental curable composition according to claim 8.

15. The method for producing a dental curable composition according to claim 1, wherein the average primary particle diameter of the spherical filler (C) is within a range of 230 nm to 350 nm.

16. The dental curable composition according to claim 8, wherein the average primary particle diameter of the spherical filler (C) is within a range of 230 nm to 350 nm.

* * * * *